United States Patent
McGaffigan (10) Patent No.: US 7,329,255 B2
(45) Date of Patent: Feb. 12, 2008

(54) SYSTEM FOR REGULATING HEATING IN A TISSUE SEALING AND CUTTING DEVICE

(75) Inventor: Thomas H. McGaffigan, Saratoga, CA (US)

(73) Assignee: Starion Instruments Corporation, Sunnyvale, CA (US)

( * ) Notice: Subject to any disclaimer, the term of this patent is extended or adjusted under 35 U.S.C. 154(b) by 0 days.

(21) Appl. No.: 10/746,213

(22) Filed: Dec. 23, 2003

(65) Prior Publication Data

US 2005/0137588 A1    Jun. 23, 2005

(51) Int. Cl.
*A61B 18/18*    (2006.01)
(52) U.S. Cl. .............................. 606/51; 606/41; 606/45
(58) Field of Classification Search ............... 606/41, 606/45–52
See application file for complete search history.

(56) References Cited

U.S. PATENT DOCUMENTS

| | | | |
|---|---|---|---|
| 4,097,718 A * | 6/1978 | Weise | 219/222 |
| 4,543,474 A | 9/1985 | Horsma et al. | |
| 5,108,392 A * | 4/1992 | Spingler | 606/51 |
| 5,369,247 A | 11/1994 | Doljack | |
| 5,451,224 A * | 9/1995 | Goble et al. | 606/48 |
| 5,624,452 A * | 4/1997 | Yates | 606/139 |
| 5,693,045 A * | 12/1997 | Eggers | 606/50 |
| 5,716,366 A | 2/1998 | Yates | |
| 6,033,399 A * | 3/2000 | Gines | 606/38 |
| 6,132,426 A | 10/2000 | Kroll | |
| 6,770,072 B1 * | 8/2004 | Truckai et al. | 606/52 |
| 2002/0052599 A1 | 5/2002 | Goble | |
| 2002/0147446 A1 | 10/2002 | Ein-Gal | |
| 2002/0165531 A1 | 11/2002 | Goble | |
| 2003/0144652 A1 * | 7/2003 | Baker et al. | 606/28 |
| 2003/0215633 A1 | 11/2003 | McClurken et al. | |
| 2003/0216733 A1 * | 11/2003 | McClurken et al. | 606/51 |

* cited by examiner

*Primary Examiner*—Michael Peffley
(74) *Attorney, Agent, or Firm*—Gordon & Rees, LLP (57) ABSTRACT

A device for handling tissue; including: a main body; a pair of opposing arms connected to the main body, the opposing arms having working surfaces thereon; a heating element disposed on one of the working surfaces; and a resistive element wired in parallel with the heating element.

17 Claims, 6 Drawing Sheets

SYSTEM FOR REGULATING HEATING IN A TISSUE SEALING AND CUTTING DEVICE

TECHNICAL FIELD

The present invention relates to medical devices for grasping and manipulating tissue, and to device for thermal cutting, sealing and welding of tissue.

BACKGROUND OF THE INVENTION

Various systems have been developed for thermal cutting, sealing and welding of tissues. An example of a novel system which combines thermal cutting, sealing and welding with tissue grasping and manipulation capabilities is provided in U.S. Pat. No. 6,626,901, owned by The Trustees of Columbia University in the City of New York.

When performing thermal cutting, sealing or welding of tissue, very precise temperatures and exposure times are required. This is due to the fact that tissues can easily be damaged by inadvertently high thermal exposure levels. Moreover, tissue sealing is accomplished at lower temperature levels than tissue cutting; and the boundary between such sealing and cutting temperatures is hard to precisely define. This is especially true when mechanical pressure is also applied to the tissue when thermally sealing or cutting the tissue. In addition, when thermally heating tissue, some portions of the tissue may be heated to a cutting temperature, whereas tissue located farther from the heat source may only be heated to a sealing temperature. Consequently, any system that is flexible enough to perform both thermal sealing and thermal cutting of tissue requires a well controlled heating system.

SUMMARY OF THE INVENTION

In preferred aspects, the present invention provides a device for handling tissue; including: a main body; a pair of opposing arms connected to the main body, the opposing arms having working surfaces thereon; a heating element disposed on one of the working surfaces; and a resistive element wired in parallel with the heating element.

As will be explained, the present invention includes a flexible heat regulating circuit that produces a desired temperature vs. time profile for the heating element disposed on the working surface(s) of the device. As such, the present system regulates heating in the device so as to supply an appropriate temperature profile to cut through tissue, or to seal tissue, or both.

Advantages of the present invention include the fact that its heating element heats at a rate that is not too fast (i.e.: it delays the onset of high temperatures by a preferred time interval as compared to the prior art). Additionally, the present system can advantageously be used to prevent the heating element from reaching too high of an operating temperature.

A further advantage of the present invention is that it regulates heating in the device by way of a simple solid-state system. Thus, it avoids the need for complex and expensive software control systems to adjust or vary current or voltage levels in its power supply. Accordingly, the present system can be used to produce a wide variety of heater temperature vs. time heating profiles while still utilizing a simple power supply (which may only be configured to supply constant current at a few pre-set levels). Alternatively, however, the power supply may be configured to supply a constant voltage, still keeping within the scope of the present invention.

A further advantage of the present invention is that it can be used to produce any of a number of different heater temperature profiles without requiring any temperature sensing elements in the heating element. Moreover, the present solid-state heat regulating system is substantially unaffected by stray electrical signals.

A further advantage of the present invention is that it is inexpensive, and can thus be made effectively job specific and disposable along with the device.

In preferred embodiments, the present system includes a heater, a resistive element and a power supply.

The resistive element may either be a positive or negative temperature coefficient (i.e.: a PTC or an NTC) element, or have a constant, temperature independent resistance. Additionally, the heating element may itself either be a positive or negative temperature coefficient (PTC or NTC) element, or have a temperature independent resistance.

In various embodiments, the pair of opposing arms of the device may comprise a pair of endoscopic shears, a pair of tweezers, forceps, or another form of tissue grasper. In various embodiments, the resistive element (of the heat regulating circuit) may be disposed in the main body, in a power cord extending from the main body, in a connector in the power cord extending from the main body, or in a current source connected to the device.

The present invention also includes a preferred method of: grasping tissue with a device having a main body and a pair of opposing arms connected thereto; and heating a working surface on one of the opposing arms by passing current through a heating element on the working surface of the arm; while simultaneously heating a resistive element wired in parallel with the heating element.

Additional optional aspects of the preferred method include heating at least one of the working surfaces to a temperature sufficient to cause sealing or cutting of tissue (or both).

Yet another additional optional aspect of the preferred method includes applying pressure to the tissue with the opposing arms of the device while heating the working surface of one of the opposing arms. Such mechanical pressure may be used not only to hold the tissue, but also to promote tissue sealing or cutting in conjunction with the thermal heat applied.

DETAILED DESCRIPTION OF THE DRAWINGS

Figure 1:
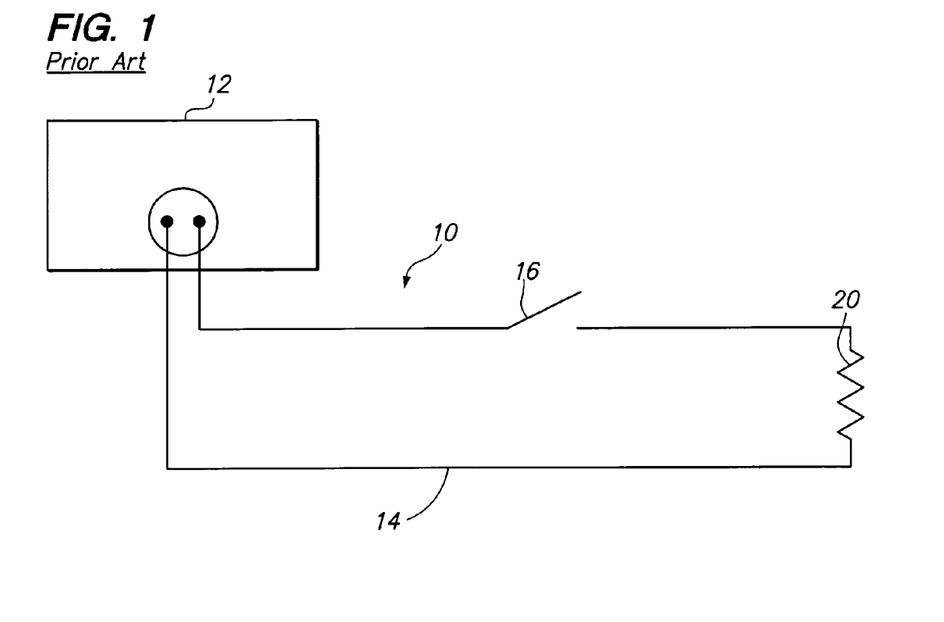
FIG. 1 is a schematic illustration of a prior art heating circuit.
Figure 2:
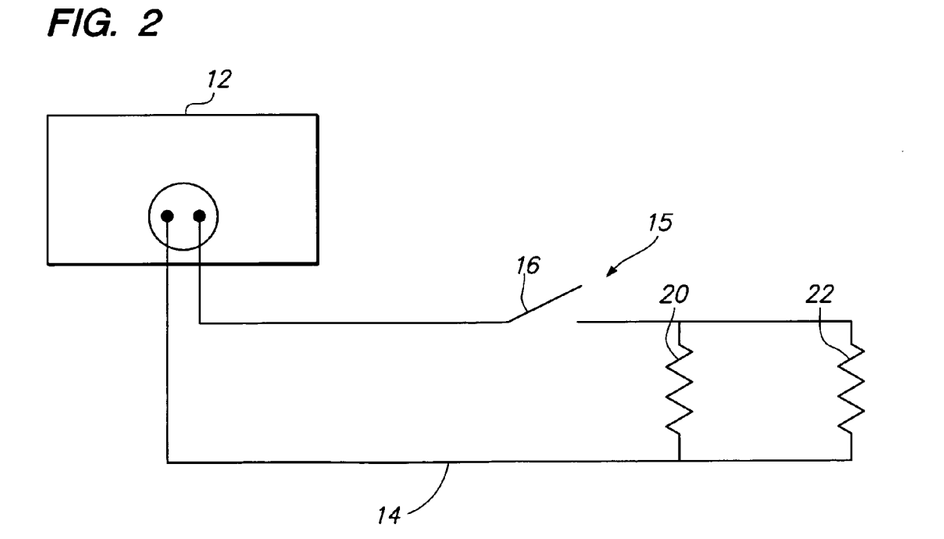
FIG. 2 is a schematic illustration of a heating circuit according to the present invention.
Figure 7:
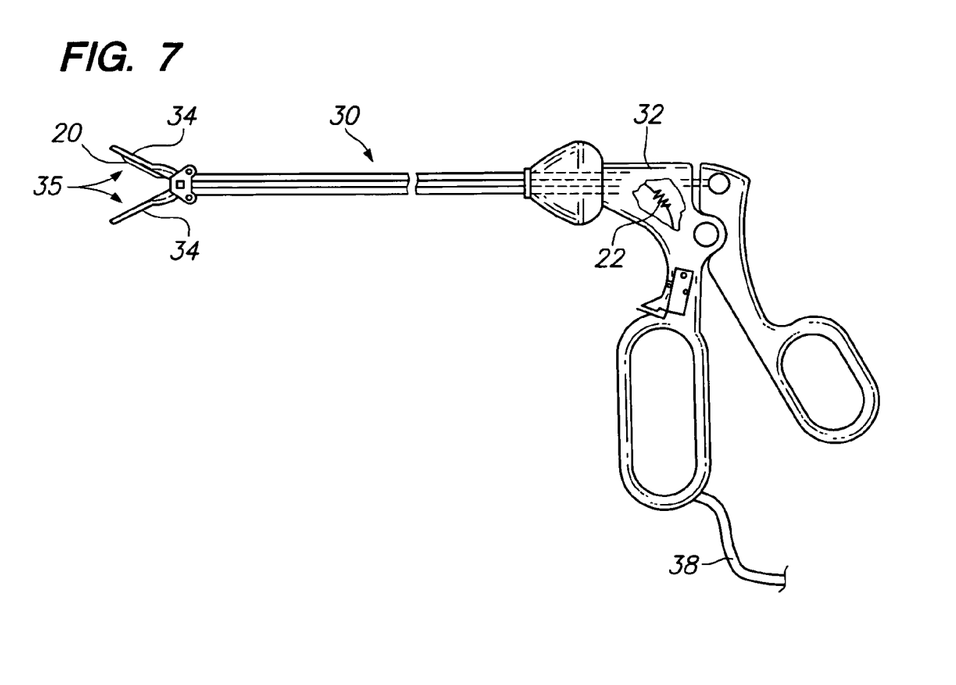
FIG. 7 is a side elevation view of an embodiment of the invention comprising a pair of endoscopic shears.
Figure 8:
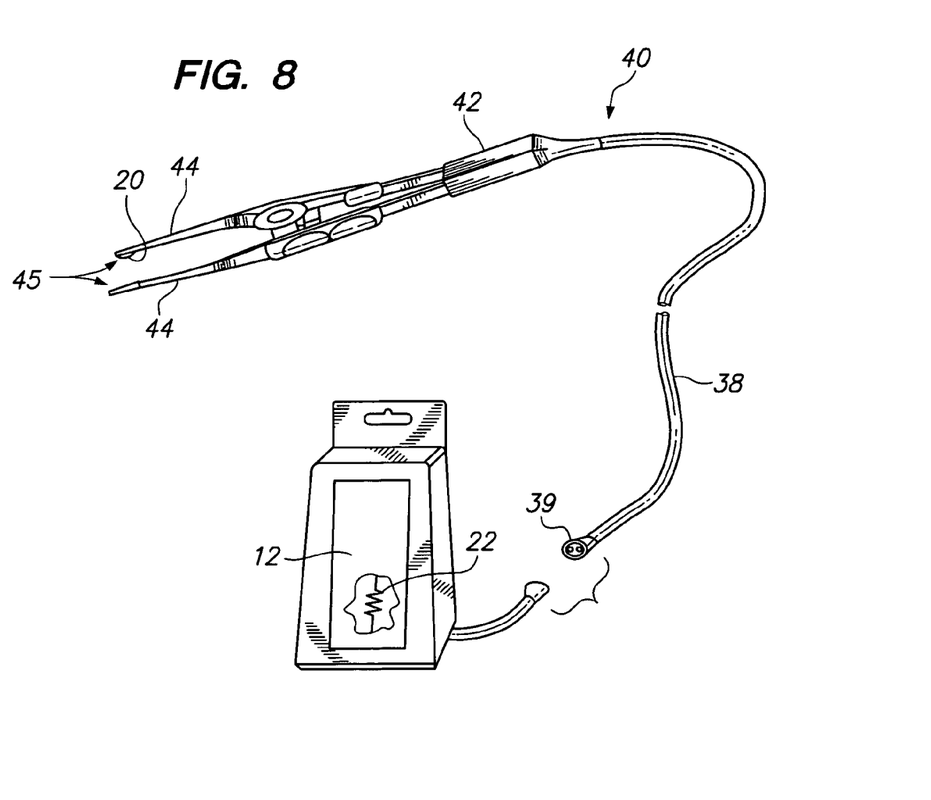
FIG. 8 is a side elevation view of an embodiment of the invention comprising a pair of tweezers.

The present invention provides a device which can be used to thermally cut, seal or weld tissue. A simplified representation of the circuitry of a prior art device is shown in FIG. 1. A simplified representation of the circuitry of the present invention is shown in FIG. 2. FIGS. 3A through 6B show temperature and power profiles for various embodiments of the present invention. Lastly, FIGS. 7 and 8 show different tissue handling devices incorporating the present invention.

As used herein, "tissue handling" may include any or all of the following: tissue manipulation, tissue thermal cutting, tissue thermal sealing or tissue thermal welding.

As used herein, a tissue "sealing temperature" is a temperature in the range of 50 to 100 degrees Celsius and a tissue "cutting temperature" is a temperature in excess of 100 degrees Celsius. However, both tissue sealing and cutting temperatures may be lower depending upon the amount of mechanical pressure that is simultaneously applied to the tissue.

Referring first to FIGS. 1 and 2, a simple prior art heating circuit (FIG. 1) is compared to the heat regulating circuit of the present invention (FIG. 2). Specifically, the prior art circuit 10 includes a current source 12, a circuit path 14, a switch 16, and a resistive heater 20.

In accordance with the present invention (FIG. 2) heat regulating circuit 15 is provided which includes all the components of circuit 10, but further including a resistive element 22 that is wired in parallel with heater 20.

In a first preferred embodiment of the invention, resistive element 22 is a positive temperature coefficient (PTC) element.

Figure 3A:
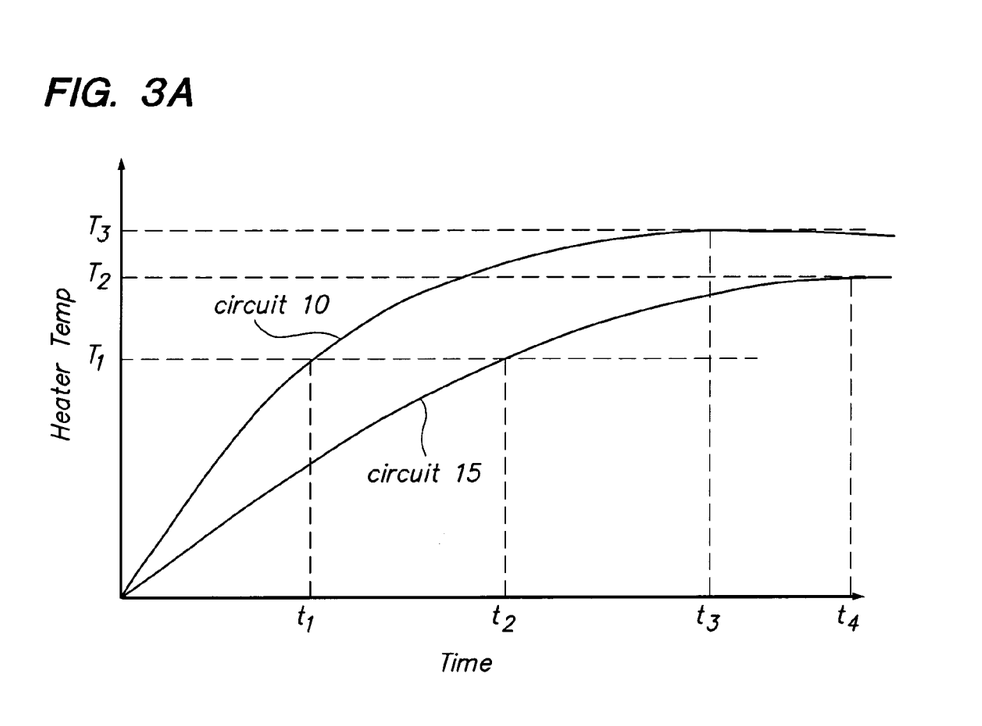
FIG. 3A is a comparison of the heater temperature vs. time profiles of the systems of FIGS. 1 and 2, when the resistive element is a positive temperature coefficient (PTC) element.
Figure 3B:
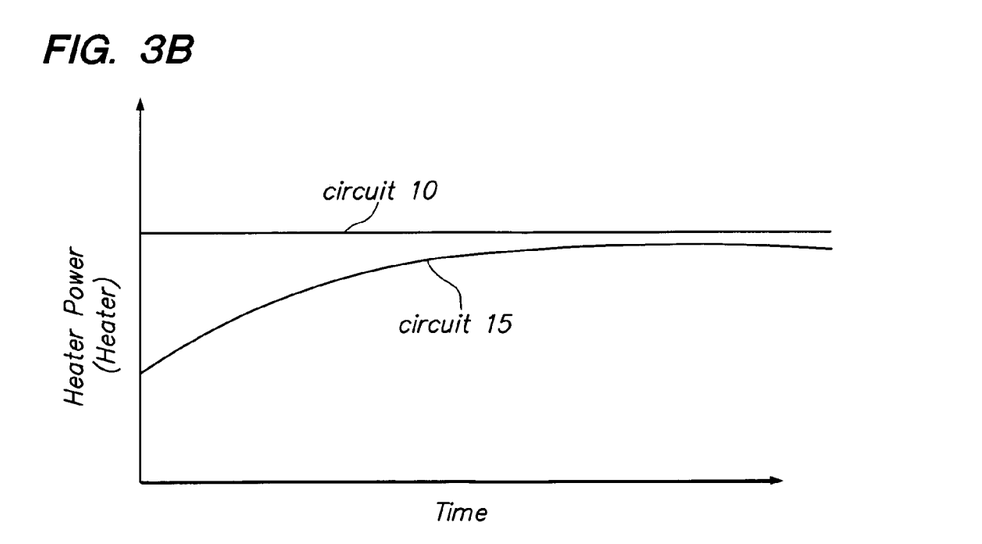
FIG. 3B is a comparison of heater power vs. time profiles corresponding to FIG. 3A.

FIG. 3A shows a temperature vs. time profile for heater 20 in the embodiment of the invention where element 22 is a positive temperature coefficient (PTC) element, and the resistance of heater 20 is temperature independent. FIG. 3B shows a power vs. time profile for heater 20 corresponding to FIG. 3A.

When element 22 is a positive temperature coefficient (PTC) element, circuit 15 will operate as follows. Current source 12 supplies current in parallel through heater 20 and PTC resistive element 22. When circuit 15 is initially activated (by closing switch 16), a relatively larger percentage of the total current (supplied by current source 12) will pass through resistive element 22 (since resistive element 22 has a lower resistance at lower temperatures). Thus, a relatively smaller percentage of the total current will initially pass through heater 20, thereby delaying the onset of heating of heater 20. Over time, the resistance of resistive element 22 will increase such that a progressively greater percentage of the total current will be directed into heater 20 (as the resistance of PTC element 22 increases as its temperature increases).

This heating delay effect can be seen in FIG. 3A where the heating profile of heater 20 in circuit 10 is compared against the heating profile of heater 20 utilizing circuit 15. Specifically, heater 20 in circuit 10 will reach temperature T1 faster than heater 20 utilizing circuit 15 will reach the same temperature T1. (IE: heater 20 reaches temperature T1 in circuit 10 at time t1, whereas heater 20 reaches temperature T1 in circuit 15 at time t2).

Delaying the onset of heating in heater 20, as shown in FIG. 3A, is particularly advantageous in that it prevents heat being applied too quickly to the tissue. Thus, the tissue is heated at a slower rate and will therefore remain in the "sealing" temperature range for a longer period of time, as opposed to rapidly entering the higher tissue "cutting" temperature range. This gives an operator more flexibility in handling the tissue during various sealing, cutting and welding tissue operations. Specifically, by increasing the amount of time during which the tissue is in the "sealing" temperature range, the ability to create an effective tissue seal is enhanced. This is desired since (when operating on blood vessels) the end of the blood vessel should first be "sealed" and then "cut". If the heater temperature is too high, the tissue will be cut prior to creating an effective seal. Unwanted bleeding from the cut end of the vessel would result.

In contrast, simply using the prior art heating circuit 10 to heat heater 20 results in a system in which tissue may be rapidly heated to a "cutting" temperature. For an operator to perform effective tissue "sealing" it may be necessary to periodically turn the system on and off to prevent excess tissue heating. As can be seen, the presence of resistive element 22 in present heat regulating circuit 15 avoids this overheating problem. Moreover, because the resistive element may be wired into the device, the operator cannot inadvertently override or defeat the desired heating profile.

It is to be understood that by varying the particular resistance characteristics of resistive element 22, the time t2 at which heater 20 reaches temperature T1 can be varied. As will be shown, resistive element 22 may optionally itself be disposed in a plurality of different interchangeable cartridges (each having different resistive elements 22) that can be placed into circuit 15. By providing different interchangeable resistive elements 22 to the operator, different heater temperature vs. time profiles can be produced.

A further advantage of having PTC element 22 present in heat regulating circuit 15 is that it limits the maximum temperature that can be reached by heater 20. For example, again looking at FIG. 3A, heater 20 achieves a maximum steady-state temperature T3 in circuit 10 (at time t3); whereas heater 20 achieves a maximum temperature T2 in circuit 15 (at time t4).

Limiting the maximum temperature T2 applied by heater 20 may be particularly advantageous in that operation at lower temperatures may prevent tissue damage. Furthermore, different tissues may have different preferred maximum operating temperatures. For example, different masses of tissue "seal" or "cut" at different temperatures from one another. As stated above, different resistive elements 22 (having different properties) may be interchanged with one another in circuit 15. Thus, different maximum temperatures T2 can be applied, depending upon the selection of different resistive elements 22. Selection of these elements may be made by the manufacturer of the device, or by the operator.

FIG. 3B shows the power vs. time profile for heater 20 in FIG. 3A. As can be seen, heater power in heat regulating circuit 15 increases over time and then levels off. In comparison, the power in heater 20 in circuit 10 remains constant over time.

The optional preferred embodiments, positive temperature coefficient (PTC) resistive element may be made of iron, tungsten or other PTC materials such as semiconductors or conductive plastics, but is not so limited.

In a second preferred embodiment of the invention, the resistance of resistive element 22 does not vary with temperature.

Figure 4A:
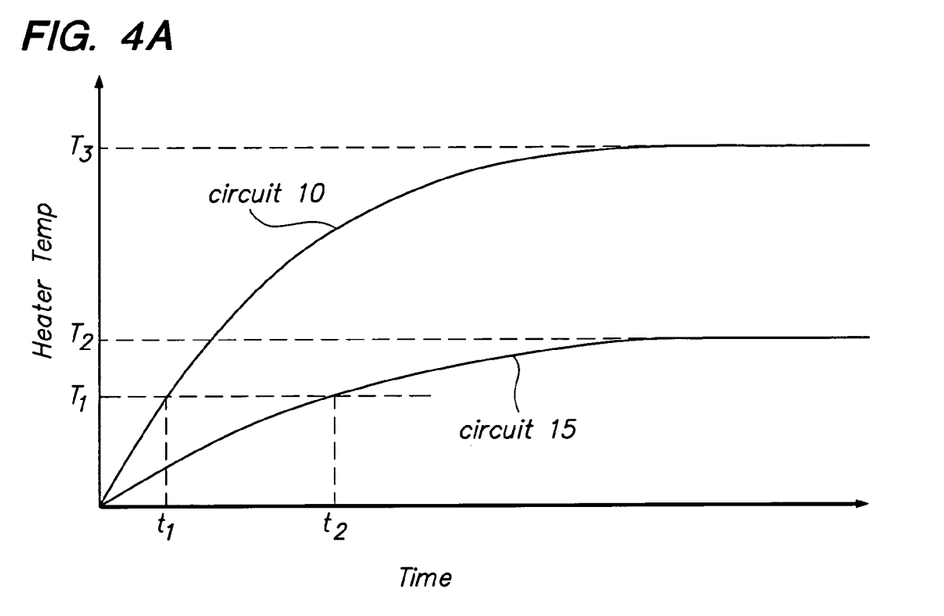
FIG. 4A is a comparison of the heater temperature vs. time profiles of the systems of FIGS. 1 and 2, when the resistive element has a temperature independent resistance.
Figure 4B:
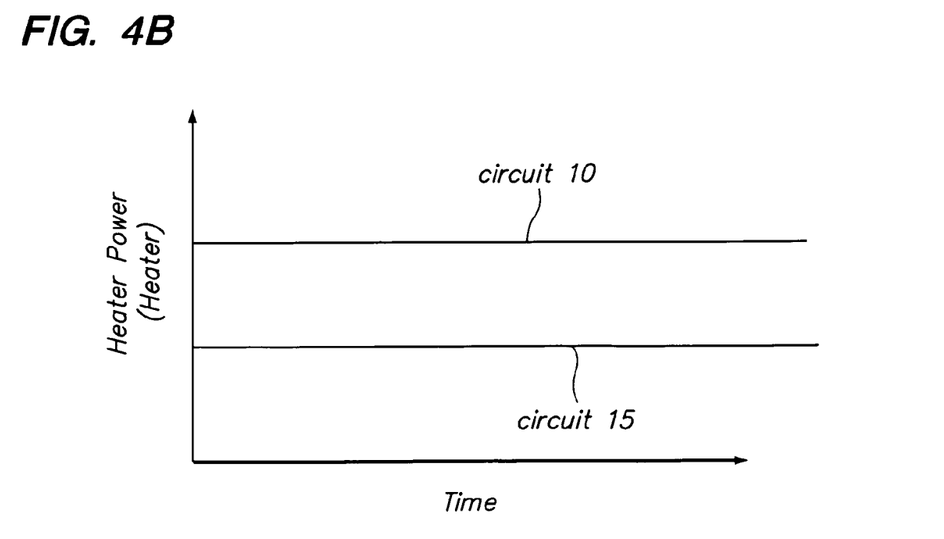
FIG. 4B is a comparison of heater power vs. time profiles corresponding to FIG. 4A.

FIG. 4A shows a temperature vs. time profile for heater 20 in the embodiment of the invention where resistive element 22 and heater 20 both have constant temperature independent resistances. FIG. 4B shows a power vs. time profile for heater 20 corresponding to FIG. 4A.

When element 22 is a constant resistance element, circuit 15 will operate as follows. Current source 12 supplies current in parallel through heater 20 and PTC resistive element 22. When circuit 15 is initially activated (by closing switch 16), portions of the total current (supplied by current source 12) will pass through heater 20 and resistive element 22. Such portions may be equal, or may be of unequal amounts (depending upon the relative resistances of resistive element 22 and heater 20). Thus, by selecting different resistive elements 22, a wide variety of heating profiles can be generated.

Similar to the positive and negative temperature coefficient (PTC and NTC) embodiments described herein, the constant resistance embodiment of resistive element 22 delays heating. This heating delay effect can be seen in FIG. 4A where the heating profile of heater 20 in circuit 10 is compared against the heating profile of heater 20 in circuit 15. Specifically, heater 20 in circuit 10 will reach temperature T1 faster than heater 20 in circuit 15 will reach the same temperature T1. (IE: heater 20 reaches temperature T1 in circuit 10 at time t1, whereas heater 20 reaches temperature T1 in circuit 15 at time t2).

The advantages of delaying the onset of heating in heater 20, are the same as those described herein in conjunction with the positive and negative temperature coefficient (PTC and NTC) embodiments of the device. Similarly, by varying the particular resistance characteristics of resistive element 22, the time t2 at which heater 20 reaches temperature T1 can be varied.

Moreover, as explained above, the maximum temperature T2 reached by heater 20 in circuit 15 can be limited to a temperature below T3 (in circuit 10). The advantages of limited maximum temperature T2 applied by heater 20 was explained above. In addition, this system provides additional fixed current levels from a single fixed output current from the power supply.

FIG. 4B shows the power vs. time profile for heater 20 in FIG. 4A. As can be seen, heater power in both heat regulating circuit 15 and in heating circuit 10 remains constant over time.

In a third preferred embodiment of the invention, resistive element 22 is a negative temperature coefficient (NTC) element.

Figure 5A:
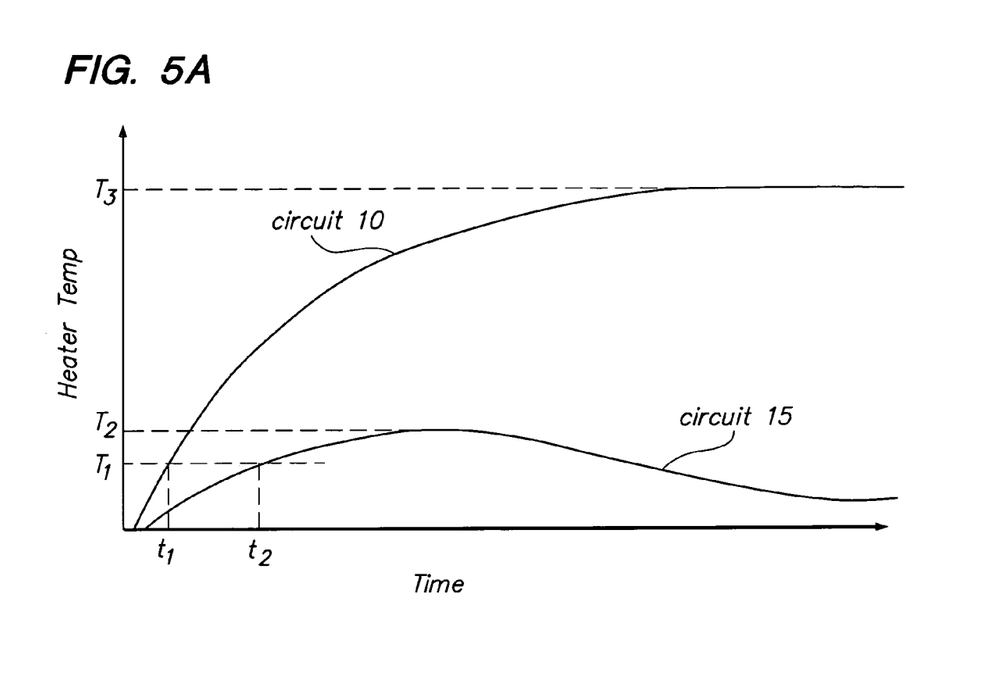
FIG. 5A is a comparison of the heater temperature vs. time profiles of the systems of FIGS. 1 and 2, when the resistive element is a negative temperature coefficient (NTC) element.
Figure 5B:
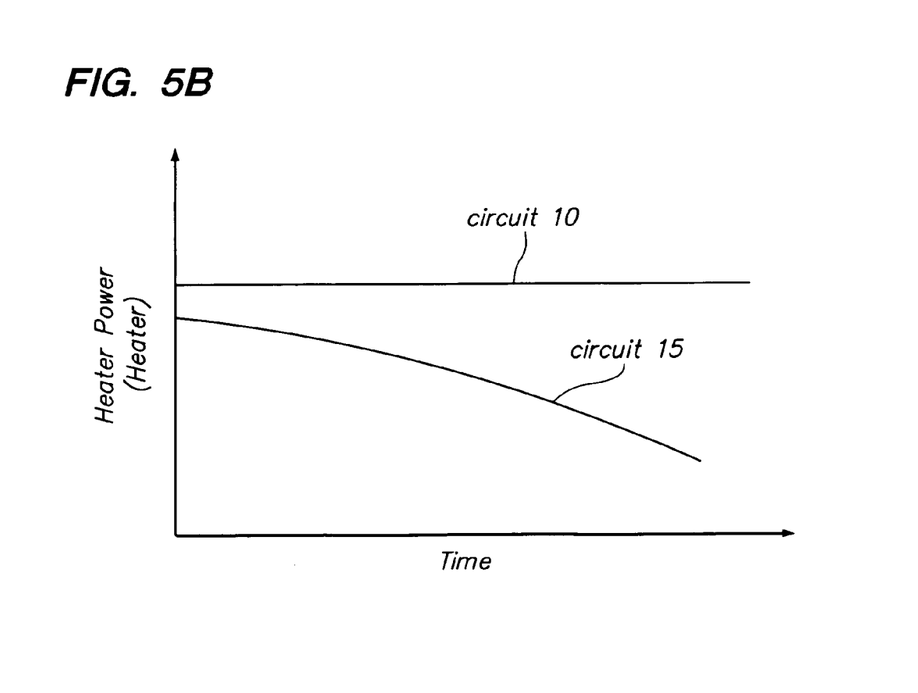
FIG. 5B is a comparison of heater power vs. time profiles corresponding to FIG. 5A.

FIG. 5A shows a temperature vs. time profile for heater 20 in the embodiment of the invention where element 22 is a negative temperature coefficient (NTC) element, and the resistance of heater 20 is temperature independent. FIG. 5B shows a power vs. time profile for heater 20 corresponding to FIG. 5A.

When element 22 is a negative temperature coefficient (NTC) element, circuit 15 will operate as follows. Current source 12 supplies current in parallel through heater 20 and NTC resistive element 22. When circuit 15 is initially activated (by closing switch 16), a relatively smaller percentage of the total current (supplied by current source 12) will pass through resistive element 22 (since resistive element 22 has a higher resistance at lower temperatures). Thus, a relatively larger percentage of the total current will initially pass through heater 20. Over time, the resistance of resistive element 22 will decrease such that a progressively smaller percentage of the total current will be directed into heater 20 (as the resistance of NTC element 22 decreases as its temperature increases).

However, similar to the positive temperature coefficient (PTC) embodiment described above, the negative temperature coefficient (NTC) embodiment will also delay the onset of heating of heater 20. This heating delay effect can be seen in FIG. 5A where the heating profile of heater 20 in circuit 10 is compared against the heating profile of heater 20 in circuit 15. Specifically, heater 20 in circuit 10 will reach temperature T1 faster than heater 20 in circuit 15 will reach the same temperature T1. (IE: heater 20 reaches temperature T1 in circuit 10 at time t1, whereas heater 20 reaches temperature T1 in circuit 15 at time t2).

The advantages of delaying the onset of heating in heater 20, are the same as those described above in conjunction with the positive temperature coefficient (PTC) and constant resistance embodiments of the device. Similarly, by varying the particular resistance characteristics of resistive element 22, the time t2 at which heater 20 reaches temperature T1 can be varied.

Moreover, as explained above, the maximum temperature T2 reached by heater 20 in circuit 15 can be limited to a temperature below T3 (in circuit 10). The advantages of limited maximum temperature T2 applied by heater 20 was explained above.

A particular advantage of having resistive element 22 be a negative temperature coefficient (NTC) element is that the maximum steady state temperature T2, applied to the tissue by heater 20 may be much lower as compared to the maximum steady state temperature T2 applied to the tissue by heater 20 when resistive element 22 is a positive temperature coefficient (PTC) element, as shown in FIG. 3A. (IE: T2 is lower in FIG. 5A than in FIG. 3A). As such, the use of a negative temperature coefficient (NTC) element as the resistive element 22 results in a heating system that applies substantially less heat that either of the above described embodiments. (IE: maximum temperature T2 in FIG. 5A is comparatively less than maximum temperature T2 in either of FIG. 3A or 4A).

This embodiment of the invention is particularly suitable when performing harvesting of arteries, where much lower levels of heating are desired in order not to damage the vessel that is being harvested.

FIG. 5B shows the power vs. time profile for heater 20 in FIG. 5A. As can be seen, heater power in heat regulating circuit 15 decreases over time and in prior art circuit 10 remains constant over time.

In the above described embodiments, the resistance of heater 20 was temperature independent. (IE: the resistance of heater 20 remained constant at different temperatures). However, the present invention is not so limited. For example, it is to be understood that the resistance of heater 20 may itself be a positive or negative temperature coefficient (PTC or NTC) element. As such, all of the nine various combinations of both heater 20 and resistive element 22 being: (1) positive temperature coefficient (PTC) elements;

negative temperature coefficient (NTC) elements; and constant resistance resistors are contemplated within the scope of the present invention.

For example, in a fourth preferred embodiment of the invention, heater 20 is a positive temperature coefficient (PTC) element, and resistive element 22 is a negative temperature coefficient (NTC) element.

Figure 6A:
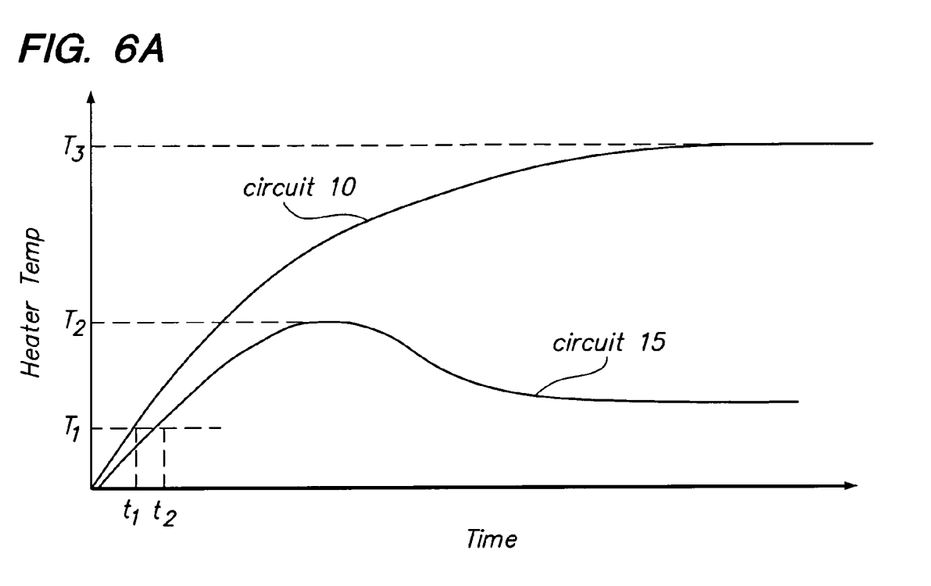
FIG. 6A is a comparison of the heater temperature vs. time profiles of the systems of FIGS. 1 and 2, when the resistive element is a negative temperature coefficient (NTC) element, and the heater is a positive temperature coefficient (PTC) element.
Figure 6B:
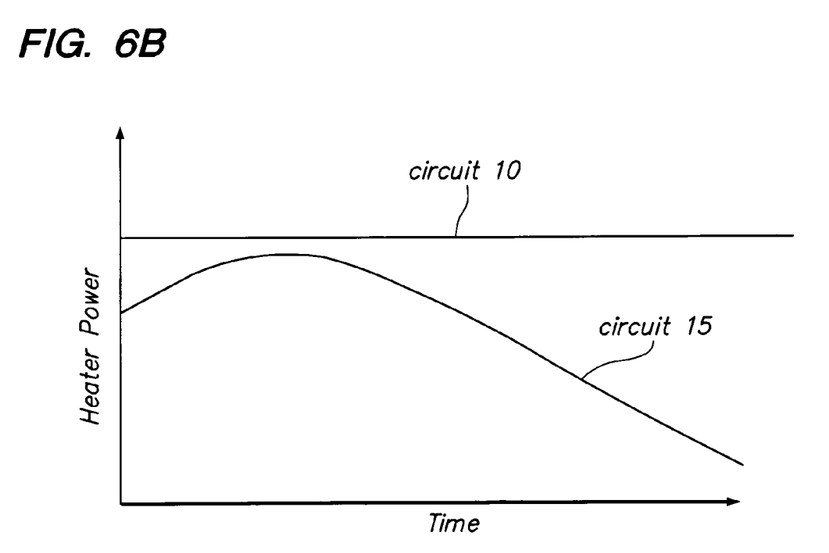
FIG. 6B is a comparison of heater power vs. time profiles corresponding to FIG. 6A.

FIG. 6A shows a temperature vs. time profile for heater 20 in the embodiment of the invention where element 22 is a negative temperature coefficient (NTC) element, and heater 20 is a positive temperature coefficient (PTC) element. FIG. 6B shows a power vs. time profile for heater 20 corresponding to FIG. 6A.

As can be seen in FIG. 6A, an advantage of this embodiment of the invention is that heater 20 reaches maximum temperature T2, and then quickly droops off. Similar to the system illustrated in FIGS. 5A and 5B, the system of FIGS. 6A and 6B is particularly suitable when performing harvesting of arteries, where much lower levels of heating are desired in order not to damage the vessel that is being harvested. The above described advantages of delaying the onset of heating (i.e. by reaching temperature T1 at time t2 as opposed to time t1) and by limiting maximum temperature (i.e.: by achieving maximum temperature T2 as opposed to T3) are also applicable. A particular advantage of the embodiment of circuit 15 as shown in FIGS. 6A and 6B is that it may drop off in temperature much faster than the system of circuit 15 as shown in FIGS. 5A and 5B.

In accordance with the present invention, heat regulating circuit 15 may be incorporated into various tissue handling systems. For example, as shown in FIG. 7, the present circuitry may be incorporated into a pair of endoscopic shears. Or, as shown in FIG. 8, the present circuitry may be incorporated into a pair of tweezers. It is to be understood that the embodiments of FIGS. 7 and 8 are merely exemplary and that the present invention may be incorporated into any tissue grasping and handling system.

Referring first to FIG. 7, a tissue handling device 30 is provided. The operation of the system shown in FIG. 7 can be understood by reference to the system described in FIG. 21 of U.S. Pat. No. 6,626,901, incorporated herein by reference in its entirety for all purposes. Specifically, FIG. 21 of U.S. Pat. No. 6,626,901 represents a system having a heating circuit 10, whereas FIG. 7 represents a mechanically similar system, instead incorporating the present heat regulating circuit 15.

Tissue handling device 30 includes a main body 32; a pair of opposing arms 34 connected to main body 32, opposing arms 34 having working surfaces 35 thereon; with heating element 20 disposed on at least one of working surfaces 25; and with resistive element 22 wired in parallel with the heating element.

As shown in cut away view in FIG. 7, resistive element 22 may be disposed within the main body 32. In preferred embodiments, resistive element 22 may be disposed within a removable cartridge in main body 32. Moreover, resistive element 22 may preferably be an elongated filament of material. An advantage of having resistive element 22 be an elongated filament is that it would cool down quickly. It is to be understood, however that he present invention is not limited only to such embodiments of resistive element 22. For example, resistive element 22 may instead be disposed within power cord 38.

The thermal mass of resistive element 22 and the materials surrounding the element dictate the heat up and reset times of the element. Thus, different resistive elements 22 can be selected to achieve different heating profiles, as desired.

Referring next to FIG. 8, a tissue handling device 40 is provided. The operation of the system shown in FIG. 8 can be understood by reference to the system described in FIG. 12 of U.S. Pat. No. 6,626,901, incorporated herein by reference in its entirety for all purposes. Specifically, FIG. 21 of U.S. Pat. No. 6,626,901 represents a system having a heating circuit 10, whereas FIG. 8 represents a mechanically similar system, instead incorporating the present heat regulating circuit 15.

Tissue handling device 40 includes a main body 42; a pair of opposing arms 44 connected to main body 42, opposing arms 44 having working surfaces 45 thereon; with heating element 20 disposed on at least one of working surfaces 25; and with resistive element 22 wired in parallel with the heating element. As show in cut away view in FIG. 8, resistive element 22 may instead optionally be disposed within current source 12. Current source 12 may be a constant-current current source. Alternatively, resistive element 22 can instead be disposed within connector 38 of power cord 38.

The present invention also includes a preferred method of handling tissue, by: grasping tissue with a device 30 or 40 having a main body 32 or 42 and a pair of opposing arms 34 or 44 connected thereto; heating a working surface 35 or 45 on one of opposing arms 34 or 44 by passing current through a heating element 20 disposed on working surface 35 or 45; while simultaneously heating a resistive element 22 wired in parallel with the heating element.

The present method also optionally includes applying pressure to the tissue with opposing arms 34 or 44 while heating working surface 35 or 45 of one of opposing arms 34 or 44. Such pressure may assist in tissue thermal sealing, cutting or welding. This may advantageously reduce the temperature (and/or time) required to perform the tissue sealing or cutting.

In optional preferred embodiments, the time required for the resistive element 22 to reach its peak temperature T2 is from 2 to 5 seconds; and the time required for the resistive element 22 to return to ambient temperature after reaching peak temperature T2 is from 1 to 3 seconds.

What is claimed is:

1. A device for cutting and sealing tissue, comprising:
a main body;
a pair of opposing arms connected to the main body, the opposing arms having working surfaces thereon;
a resistive heating element disposed on one of the working surfaces; and
a resistive element wired in parallel with the resistive heating element, the resistive element being disposed in a portion of the device such that the resistive element does not contact the tissue, wherein the resistive element delays the onset of heating and limits maximum heating to increase a time period during which temperatures are in a tissue sealing range, and wherein the resistive heating element is a positive temperature coefficient (PTC) element or a negative temperature coefficient (NTC) element.

2. The device of claim 1, wherein the resistive element has a temperature independent resistance.

3. The device of claim 1, wherein the heating element is a positive temperature coefficient (PTC) element.

4. The device of claim 1, wherein the heating element is a negative temperature coefficient (NTC) element.

5. The device of claim 1, wherein the heating element has a temperature independent resistance.

6. The system of claim 1, wherein the pair of opposing arms comprise a pair of tweezers.

7. The system of claim 1, further comprising: a current source configured to pass current in parallel through the resistive element and the heating element.

8. The system of claim 7, wherein the power source supplies a constant current.

9. The system of claim 7, wherein the power source supplies a constant voltage.

10. The system of claim 7, wherein the resistive element is disposed in the current source.

11. The device of claim 1, wherein the pair of opposing arms comprise a pair of forceps.

12. The system of claim 1, wherein the pair of opposing arms comprise a grasper.

13. The system of claim 1, wherein the resistive element is disposed in the main body.

14. The system of claim 1, further comprising: a power cord extending from the main body, wherein the resistive element is disposed in the power cord.

15. The system of claim 1, further comprising: a power cord extending from the main body, the power cord having a connector at its end, wherein the resistive element is disposed in the connector.

16. A system for regulating heating is a tissue cutting and sealing device, comprising:

a resistive heating element;

a resistive element wired in parallel with the heating element, the resistive element being positioned such that the resistive element does not contact the tissue during operation, wherein the resistive heating element is a positive temperature coefficient (PTC) element or a negative temperature coefficient (NTC) element; and a power supply, wherein the resistive element delays the onset of heating and limits maximum heating to increase a time period during which temperatures are in a tissue sealing range.

17. The system of claim 16, wherein the resistive element has a temperature independent resistance.

* * * * *